United States Patent [19]

Koszinowski et al.

[11] Patent Number: 4,968,615
[45] Date of Patent: Nov. 6, 1990

[54] DEOXYRIBONUCLEIC ACID SEGMENT FROM A VIRUS

[75] Inventors: Ulrich H. Koszinowski; Günther M. Keil, both of Tübingen, Fed. Rep. of Germany; Karoline Dorsch-Häsler, Zürich; Walter Schaffner, Weiningen, both of Switzerland

[73] Assignee: CIBA-GEIGY Corporation, Ardsley, N.Y.

[21] Appl. No.: 810,470

[22] Filed: Dec. 18, 1985

[51] Int. Cl.$^5$ .................. C12N 15/00; C12N 15/11; C12N 15/86; C12P 19/34
[52] U.S. Cl. .................. 435/172.3; 536/27; 435/91; 435/69.1; 435/70.1
[58] Field of Search .................. 435/68, 70, 91, 235, 435/253, 172.3, 3, 7; 935/32, 34, 36, 41, 56, 57, 71

[56] References Cited

PUBLICATIONS

Poster of USEB meeting, Geneva, Mar. 23, 1985, Experientia 41 (1985) 798, Abstr. of USSEB meeting.
Ebeling, A., et al. J. Virol 47, 421–433 (1983).
Mercer, J. A. et al. Virology 129, 94–106 (1983).
Marks, J. R. et al., Virology 131, 247 ∝ 254 (1983).
Keil, G. M., et al. J. Virol, 50, 784–795 (1984).
Boshart, M. et al., Cell 41, 521–530 (1985).

Primary Examiner—Richard A. Schwartz
Assistant Examiner—S. L. Nolan
Attorney, Agent, or Firm—JoAnn Villamizar; Irving N. Feit

[57] ABSTRACT

Deoxyribonucleic acid (DNA) molecules consisting of or recombinant DNA molecules containing transcription enhancers from murine cytomegalovirus (MCMV) which can be used to enhance the transcription of structural genes in eukaryotic cells.

25 Claims, 7 Drawing Sheets

```
         PstI (~-2100)                           -835
              ↓                                   ↓
         ....................................ATTGTACCTGCCCGT
-820
  ↓
    ACATAAGGTCAATAGGGGTGAATCAACGGAAAAGTCCCATTGGAGCCAAGTACACTGCGT
-760
  ↓
    CAATAGGGACTTTCCATTGGGTTTTGCCCAGTACATAAGGTCAATAGGGGATGAGTCAAT
-700
  ↓
    GGGAAAAACCCATTGGAGCCAAGTACACTGACTCAATAGGGACTTTCCATTGGGTTTTGC
-640
  ↓
    CCAGTACATAAGGTCAATAGGGGGTGAGTCAACAGGAAAGTTCCATTGGAGCCAAGTACA
-580                                                      P1
  ↓                                                        ↓
    TTGAGTCAATAGGGACTTTCCAATGGGTTTTGCCCAGTACATAAGGTCAATGGGAGGTAA
-520
  ↓
    GCCAATGGGTTTTTCCCATTACTGGCACGTATACTGAGTCATTAGGGACTTTCCAATGGG
-460              B2
  ↓                ↓
    TTTTGCCCAGTACATAAGGTCAATAGGGGTGAATCAACAGGAAAGTCCCATTGGAGCCAA
-400
  ↓
    GTACACTGAGTCAATAGGGACTTTCCATTGGGTTTTGCCCAGTACAAAAGGTCAATAGGG
-340
  ↓
    GGTGAGTCAATGGGTTTTTCCCATTATTGGCACGTACATAAGGTCAATAGGGGTGAGTCA
-280
  ↓
    TTGGGTTTTTCCAGCCAATTTAATTAAAACGCCATGTACTTTCCCACCATTGACGTCAAT
-220  P1
  ↓   ↓
    GGGCTATTGAAACTAATGCAACGTGACCTTTAAACGGTACTTTCCCATAGCTGATTAATG
-160          XhoI                                         B2
  ↓            ↓                                            ↓
    GGAAAGTACCGTTCTCGAGCCAATACACGTCAATGGGAAGTGAAAGGGCAGCCAAAACGT
-100
  ↓
    AACACCGCCCCGGTTTTCCCTGGAAATTCCATATTGGCACGCATTCTATTGGCTGAGCTG
 -40      tata box              +1 (initiation)
  ↓        ↓  ↓                       ↓
    CGTTCACGTGGGTATAAGAGGCGCGACCAGCGTCGGTACCGTCGCAGTCTTCGGTCTGAC
 +21                   +50                   (+101) PstI
  ↓                     ↓                         ↓
    CACCGTAGAACGCAGAGCTCCTCGCTGCAG...............
```

FIG. 3A

DEOXYRIBONUCLEIC ACID SEGMENT FROM A VIRUS

FIELD OF THE INVENTION

The invention relates to deoxyribonucleic acid (DNA) molecules consisting of or recombinant DNA molecules containing transcription enhancers useful in genetic engineering technique, especially to DNA fragments obtainable from murine cytomegalovirus (MCMV) which can be used to enhance the transcription of structural genes in eukaryotic cells.

BACKGROUND OF THE INVENTION

The present invention was prepublished by the inventor on March 28, 1985, on a poster at the Union of Suisse Societies of Experimental Biology (USSEB) meeting, Geneva, Switzerland, [cf. abstract in Experientia 41 (1985), 798].

Transcription enhancers are cis-acting DNA elements that are able to activate RNA polymerase II-transcribed genes in either orientation from a distance of up to several kbp from the promoter site (ref. 5,6), even when located downstream of the transcribed sequences (ref. 5; for reviews, see refs. 7–9). Originally detected in papovaviruses, their presence has since been demonstrated in a number of animal viruses, including herpesviruses such as herpes simplex (ref. 10), human cytomegalovirus (HCMV) (ref. 11), and Herpesvirus saimiri (ref. 12). Some enhancers, e.g. the enhancers from simian virus 40 (SV 40) and HCMV, can function in a number of different cell types, while others show a distinct host-cell preference. Enhancers that are associated with cellular genes, e.g. immunoglobulin genes (ref. 13–15), rat insulin (ref. 16), and a murine class II major histo-compatibility antigen gene (ref. 17), are often stricly cell-type specific.

It is envisaged that transcription enhancers can be used as important tools in genetic engineering experiments for the construction of expression systems for virus infectable eukaryotic cells. Such cells, especially vertebrate cells, transformed with a vector containing such enhancer and a structural gene would have higher transcription rates for messenger ribonucleic acids (mRNA) and hence can be expected to express more of the desired polypeptide encoded by the structural gene. As some of the known enhancers are not working in certain cells and the transcription rates are not necessarily high, there is a need for further enhancers able to fill this gap.

OBJECT OF THE INVENTION

It is an object of this invention to provide novel DNA molecules containing transcription enhancers with an extremely high transcription rate which can be used in eukaryotic, especially vertebrate cells. Advantageously the enhancers of the invention are attached to their naturally associated promoter.

DETAILED DESCRIPTION OF THE INVENTION

Surprisingly such an enhancer was identified in murine cytomegalovirus. Accordingly, the invention concerns a DNA molecule consisting of, or a recombinant DNA molecule containing transcription enhancer DNA from the upstream region of the major immediate early (IE) gene of murine cytomegalovirus (MCMV) or an enhancer-active mutant thereof, and optionally promoter sequences and/or other flanking sequences. Such DNA-molecules are useful in eukaryotic expression systems.

Murine cytomegalovirus (MCMV) is a member of the highly diverse group of herpesviruses. Even among cytomegaloviruses of different host species there can be wide variation. For example, MCMV differs considerably from the human cytomegalovirus (HCMV) with respect to biological properties, immediate early (IE) gene organization, and overall nucleotide sequence. The 235-kilobase-pair (kbp) genome of MCMV also lacks large internal and terminal repeats characteristic of HCMV. Accordingly, no isomeric forms of the MCMV genome exist (ref. 1,2).

As in other members of the herpes group, MCMV gene expression is temporally regulated. IE genes are expressed in the absence of protein synthesis, early gene products depend on the synthesis of at least one IE gene product, and late RNAs are synthesized after the onset of viral DNA synthesis. MCMV has one major IE region (ref. 3,4). This region codes for one major 2.75-kb and five minor polyadenylated IE RNAs. Low levels of IE transcripts have also been detected from both termini of the genome (ref. 3,4). In an attempt to answer the question of how transcription is regulated, the present transcription enhancers that control the IE promoter have been identified.

Figure 1:
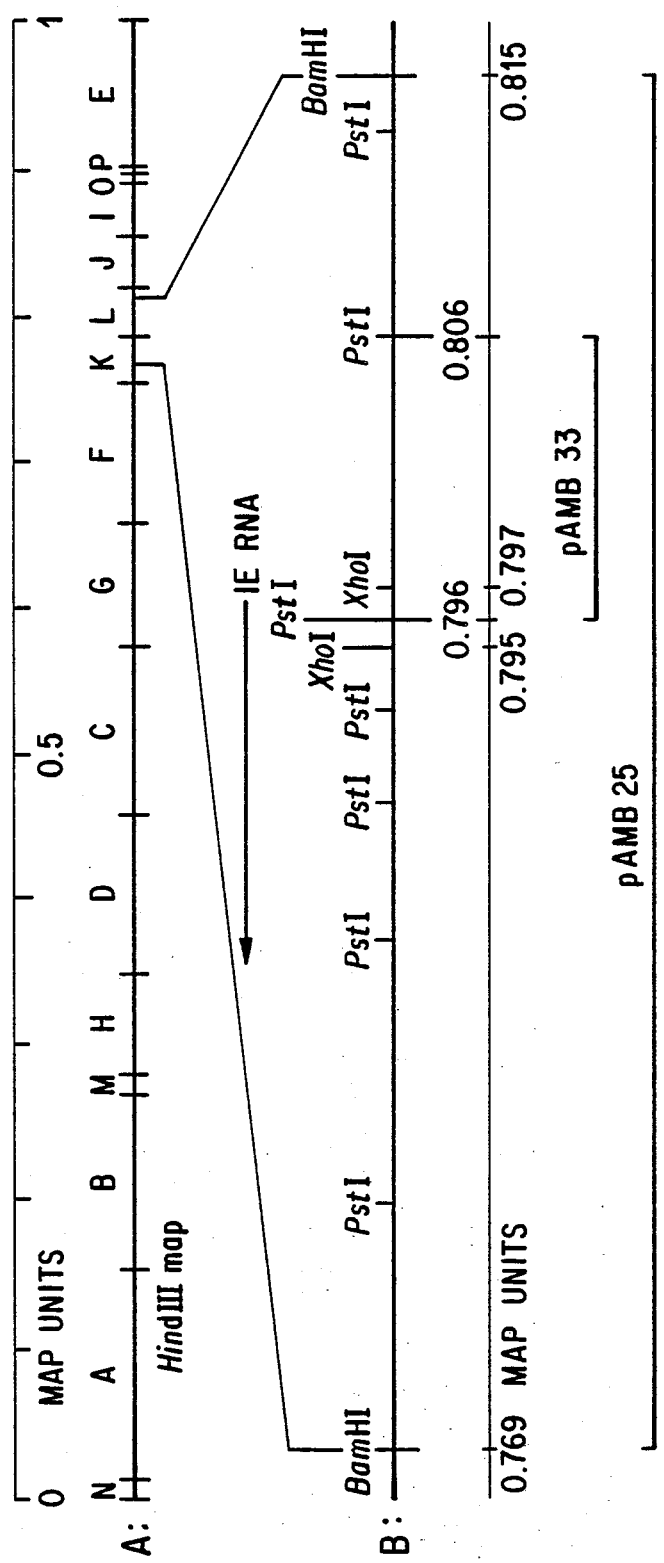

The transcription enhancer DNA from the upstream region of the major IE gene of MCMV is defined as the DNA sequence located between about 0.806 and about 0.796 map units, i.e. within the PstI restriction fragment. A promoter is any DNA sequence where RNA polymerase initiates transcription, and is preferably the homologous MCMV- IE promoter. The IE promoter region extends from the PstI site at about position +100 to about position −100 from the transcription initiation site (+1) (FIG. 1). Other flanking sequences include heterologous promoters and linkers. Enhancer-active mutants of said enhancer DNA are such DNAs wherein one or more nucleotides have been replaced by other nucleotides without loosing the enhancer activity of the entire DNA sequence.

Figure 2:
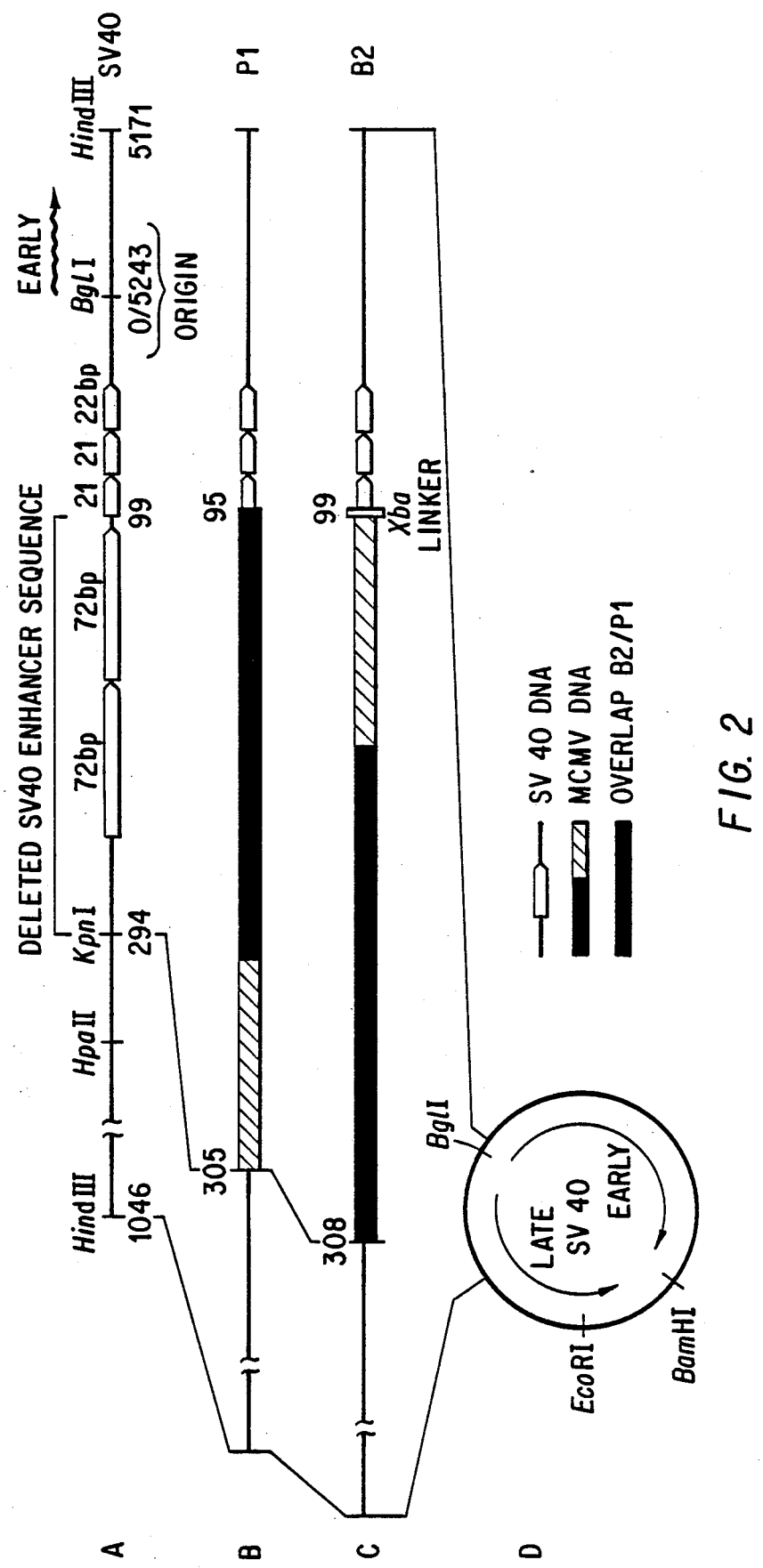

Another embodiment are DNA molecules consisting of, or recombinant DNA molecule containing, the HindIII C fragment from the recombinant SV40-MCMV P1 clone (FIG. 2, B) containing the MCMV enhancer which originates from a cotransfection of SV40 enhancer trap DNA and the MCMV-specific 2.27-kb PstI fragment of the MCMV genome or from SV40-MCMV B2 clone (FIG. 2, C) containing the MCMV enhancer which originates from a cotransfection of SV′enhancer trap DNA and the MCMV-specific 10.8-kb PstI fragment of the MCMV genome.

Other exemplifications are DNA molecule consisting of, or recombinant DNA molecule containing, the DNA sequence of the formula

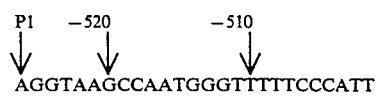

-continued

```
-500        -490        -480        -470        -460        -450
 ↓           ↓           ↓           ↓           ↓           ↓
   ACTGGCACGTATACTGAGTCATTAGGGACTTTCCAATGGGTTTTGCCCAGTACATAAGGT
-440        -430        -420        -410        -400        -390
 ↓           ↓           ↓           ↓           ↓           ↓
   CAATAGGGGTGAATCAACAGGAAAGTCCCATTGGAGCCAAGTACACTGAGTCAATAGGGA
-380        -370        -360        -350        -340        -330
 ↓           ↓           ↓           ↓           ↓           ↓
   CTTTCCATTGGGTTTTGCCCAGTACAAAAGGTCAATAGGGGGTGAGTCAATGGGTTTTTC
-320        -310        -300        -290        -280        -270
 ↓           ↓           ↓           ↓           ↓           ↓
   CCATTATTGGCACGTACATAAGGTCAATAGGGGTGAGTCATTGGGTTTTTCCAGCCAATT
-260        -250        -240        -230        -220        P1
 ↓           ↓           ↓           ↓           ↓       ↓
   TAATTAAAACGCCATGTACTTTCCCACCATTGACGTCAATGGGCT
``` or

```
                                                              B2
                                                              ↓
                                                              GT
-440        -430        -420        -410        -400        -390
 ↓           ↓           ↓           ↓           ↓           ↓
   CAATAGGGGTGAATCAACAGGAAAGTCCCATTGGAGCCAAGTACACTGAGTCAATAGGGA
-380        -370        -360        -350        -340        -330
 ↓           ↓           ↓           ↓           ↓           ↓
   CTTTCCATTGGGTTTTGCCCAGTACAAAAGGTCAATAGGGGGTGAGTCAATGGGTTTTTC
-320        -310        -300        -290        -280        -270
 ↓           ↓           ↓           ↓           ↓           ↓
   CCATTATTGGCACGTACATAAGGTCAATAGGGGTGAGTCATTGGGTTTTTCCAGCCAATT
-260        -250        -240        -230        -220        -210
 ↓           ↓           ↓           ↓           ↓           ↓
   TAATTAAAACGCCATGTACTTTCCCACCATTGACGTCAATGGGCTATTGAAACTAATGCA
-200        -190        -180        -170        -160        -150
 ↓           ↓           ↓           ↓           ↓           ↓
   ACGTGACCTTTAAACGGTACTTTCCCATAGCTGATTAATGGGAAAGTACCGTTCTCGAGC
-140        -130        -120        -110        B2
 ↓           ↓           ↓           ↓       ↓
   CAATACACGTCAATGGGAAGTGAAAGGGCAGCCAAAACGT
```

The recombinant DNA molecules of the present invention may or may not contain the MCMV IE promoter, and may contain instead any other eukaryotic promoter, and in addition may contain a heterologous structural gene, and/or other flanking sequence, such as linkers, DNA sequence originating from the enhancer trap used, signal sequence for the structural gene and/or other sequences originating during construction of vectors containing the present MCMV enhancer sequences.

The invention concerns further a process for the production of a DNA molecule consisting of, or a recombinant DNA molecule containing transcription enhancer DNA from the upstream region of the major immediate early (IE) gene of murine cytomegalovirus (MCMV) or an enhancer-active mutant thereof, and optionally promoter sequences and/or other flanking sequences, characterized in (a) fragmenting DNA molecules from the IE region of MCMV or purified total MCMV, cotransfecting the obtained DNA fragments with enhancerless genomes of another virus into eukaryotic cells, isolating from the transfected cells viable recombinant viruses containing DNA molecules showing enhancer activity and isolating from the obtained viral DNA the inserted DNA originating from MCMV, or (b) determining the structure of the inserted MCMV DNA molecule and synthesizing the inserted MCMV DNA molecule, an enhancer-active fragment or enhancer-active mutant thereof, (c) or fragmenting purified total MCMV DNA or DNA molecules from the IE region of the MCMV DNA by sonication or by treatment with at least one restriction enzyme and/or optionally an exonuclease, optionally followed by treatment with a DNA polymerase, optionally followed by cloning in a suitable vector, whereby the enhancer DNA is identified by hybridization to DNA containing a sequence of the IE enhancer or IE promoter, and, if desired, preparing a recombinant DNA molecule containing the obtainable transcription enhancer DNA or enhancer-active mutant thereof.

The transcription enhancer DNAs of the present invention have been identified by the "enhancer trap" method. The fact that in SV40 the enhancer can be substituted by heterologous enhancers has led to the development of the SV40 "enhancer trap," whereby enhancerless SV40 DNA regains infectivity by incorporating an exogeneous enhancer (18). The enhancer trap allows the selection of a transcription enhancer from a large excess of DNA. By cotransfecting enhancer trap DNA and the entire MCMV genome or DNA from its major IE region, it is possible to recover a very strong transcription enhancer upstream of the major IE region of MCMV.

The MCMV enhancer has been sequenced and its location with respect to the IE region has been determined. Sequence analysis revealed a complex arrangement of repeats and also short DNA motifs found in other enhancers, which presumably are binding sites for nuclear proteins.

A preferred enhancer trap, i.e. the enhancer-less genom of a virus, is the known XbaI and KpnI-digested enhancer trap DNA of SV40 (clone pET-1, ref. 18), however, also other enhancer traps, e.g. as described by Tognoni et al. (ref. 34) or the enhancer-dependant adenovirus-promoter-driven, modular dihydrofolate reductase (DHFR) gene in plasmid pAdD26SV(A) (ref. 38), can be used.

The MCMV DNA molecules, i.e. the entire MCMV DNA or fragments thereof, used for cotransfection can be obtained by isolation and purification of MCMV DNA or by digestion thereof with various restriction enzymes, e.g. with PstI, KpnI or SacI, or especially by sonication of the entire MCMV genome or parts thereof, e.g. the 10.8 BamHI fragment. The DNA fragments obtained by sonication or by treatment with a suitable restriction enzyme may be isolated and/or cloned in a suitable vector, such as pBR322, pUC18, pUC19 and the like. Optionally the obtained fragments can be further processed by treatment with an exonuclease, e.g. BAL31, and/or a DNA polymerase, e.g. E.coli polymerase I or T4 DNA polymerase in order to lengthen or shorten the DNA chains. The source of MCMV can be strain Smith (ATCC VR-194). Propagation of MCMV in BALB/c mouse embryo fibroblasts, purification of MCMV virus particles, viral DNA, and viral RNA have been described (1,4).

As the MCMV enhancer shows no obvious cell preference, it can be expressed in a number of different eukaryotic cell types. Accordingly, for cotransfection there can be used any eukaryotic cell types, especially vertebrate cells, e.g. mouse 3T3 fibroblasts or L-cells, human cells, such as Hela, HEp2, KB or WISH cells, monkey vero or kidney CV-1 cells, frog kidney B cells, or or Chinese hamster ovary cells (CHO).

Cotransfections can be performed by any of the known methods, e.g. by direct gene transfer or the DEAE-dextran technique (ref. 35) and especially by the calcium phosphate technique (ref. 18).

The cotransfected cells are screened by extracting the recombinant viral DNAs and cloning into a plasmid, e.g. the BamHI site of pBR327, according to known methods, for example as described in ref. 1 and 4, and analyzed by known methods, for example as described in ref. 18, as to their lytic growth potential. In general the transfected cells, e.g. the CV-1 cells, containing MCMV enhancer DNA begin to lyse 2-3 weeks after transfection, indicating that a viable virus, e.g. SV-40 virus, had been generated.

For example, recombinant SV40-MCMV viral DNAs are isolated and cloned in the bacterial plasmid pBR327. Individual recombinant virus clones are reclaimed from the plasmid and tested for viability by transfection into monkey CV-1 cells using the DEAE-dextran method. By this method 15 of 16 clones originating from transfection with the entire MCMV genome, 8 of 8 clones originating from the pAMB25 transfection, and 6 of 8 clones originating from the pAMB33 transfection, were viable and lysed CV-1 cells 12-16 days after transfection. This is about the same time it takes to lyse the cells when transfection is performed with SV40 wild-type DNA or SV40-HCMV recombinant DNA (ref. 11).

By Southern blot hybridization, it was shown that all the analyzed clones hybridized exclusively to the PstI fragment cloned in plasmid pAM33 spanning map units 0.796-0.806 on the MCMV genome.

In order to determine the nucleotide sequence of the MCMV enhancer sequence the recombinant MCMV DNAs are recovered from the clones and sequenced.

For example, two fast-growing MCMV-SV40 recombinant clones were chosen for further analysis: B2, derived from cotransfection of the 10.8-kbp pAMB25 fragment with enhancer trap DNA, and P1, derived from the 2.27-kbp pAMB33 transfection. Clone B2 contained a 342-bp MCMV fragment ligated to the ends of the enhancer trap, and clone P1 contained a 311-bp MCMV segment (FIG. 2), overlapping with the B2 fragment by 227 bp. In both cases, on either side of the enhancer trap 5-15 bp of SV40 DNA were deleted, presumably by exonuclease digestion within the cell prior to ligation. No deviation from the wild-type SV40 sequence was found withing 300 bp of flanking enhancer trap DNA.

Figure 3B:
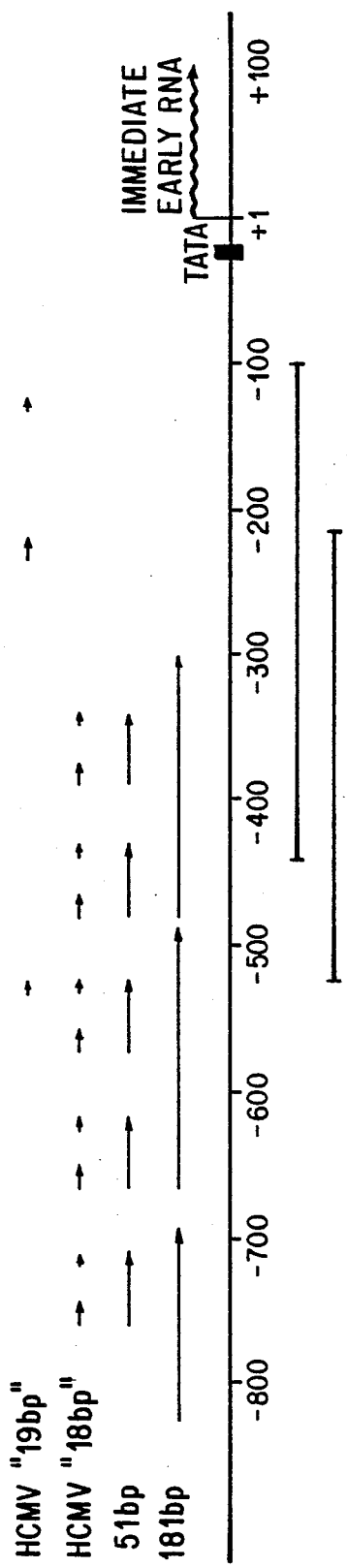

To accurately determine the location of the enhancer within the MCMV PstI fragment, the sequence of 835 bp 5' to the cap site, and 31 bp 3' to the cap site of the major IE region was analyzed (FIG. 3). The analysis revealed that the B2 and P1 enhancers are both colinear with the genomic DNA of MCMV and have not suffered any secondary sequence alterations.

Having determined the structural sequence of the MCMV enhancer DNA insert, it is possible to synthesize enhancer-active fragments or enhancer-active mutants thereof by methods known in the art, e.g. by chemical synthesis or recombinant cloning techniques.

Likewise, DNA molecules containing the obtainable transcription enhancers, especially vectors, such as plasmids, viral vectors or cosmids, containing a promoter in proper reading frame with a structural gene and other sequences necessary for successful transformation, proliferation, transcription and finally translation into useful polypeptides, can be prepared by common techniques known in the art.

Figure 4A:
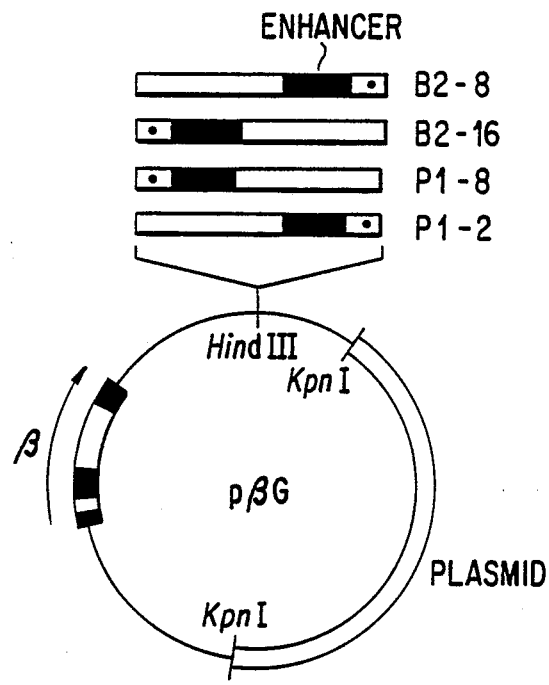
Figure 4B:
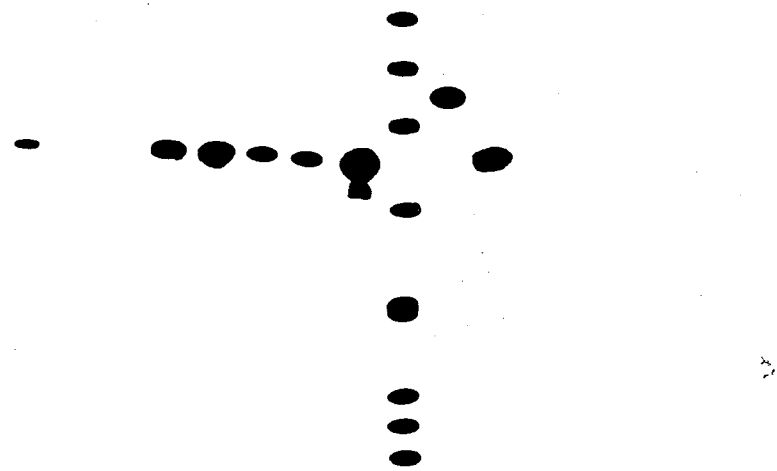
Figure 5:
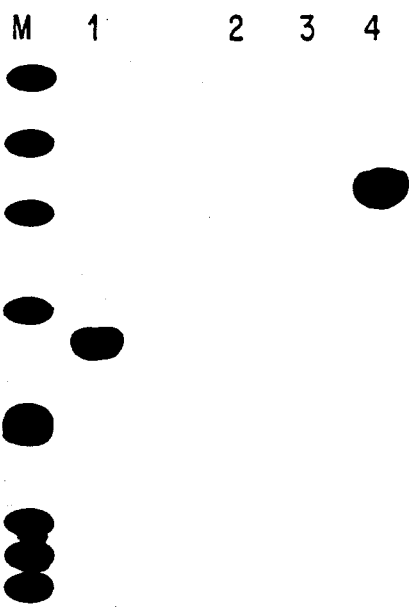

The functional analysis of the obtainable enhancer DNAs according to the invention can be carried out by methods known in the art. For example, it is known that classical enhancers can stimulate transcription of a heterologous test gene in an orientation-independent way, even when located downstream of that gene. To test whether the MCMV enhancer satisfies that definition, a HindIII fragment from the recombinant MCMV-SV40 clones B2 and P1 containing MCMV enhancer sequences (ranging from position 5171 to 1046 on the SV40 map) was cloned in either direction downstream of the rabbit β-globin gene in the plasmid pBG (ref. 26) (FIG. 4A). Clones containing the enhancer from the SV40 wild type and the previously analyzed strong enhancer from HCMV were used for comparison. Transient expression of globin messenger RNA in HeLa cells was measured by an S1 nuclease assay of cytoplasmic RNA, using a β-globin-specific probe. The B2 and P1 enhancer segments of MCMV, show an activity which is similar to the enhancer from HCMV, and are about two to five times more active than the SV40 wild-type enhancer (FIG. 4B). When a pβG clone lacking an enhancer was used as a control, no transcription of the β-globin gene was detected. Like other enhancers (reviewed in refs. 7–9; see also refs. 11 and 18), the MCMV enhancer can be inserted in either orientation, yet β-globin gene expression is stimulated to the same extent (FIG. 4B). Thus, the MCMV enhancer meets all the criteria of a strong transcription enhancer.

Accordingly, the present invention concerns also the use of the present enhancer in a process for improving eukaryotic expression systems, which comprises incorporation of a DNA molecule consisting of, or a recombinant DNA molecule containing, transcription enhancer DNA from the upstream region of the major immediate early (IE) gene of murine cytomegalovirus (MCMCV) or an enhancer active mutant thereof upstream or downstream of the structural gene or of the regulation region.

The enhancer DNA is preferably incorporated as close as possible to the promoter, usually less than 3000 bp upstream or, if placed downstream of the structural gene, less than 7000 bp away from the promoter.

The invention is further illustrated in the following detailed Examples and Figures which, however, should not be construed as a limitation thereof.

EXAMPLE 1

Unless specified otherwise, established laboratory techniques as described by Maniatis et al (ref 37) are used.

(a) Preparation of the enhancer trap

Figure 6:
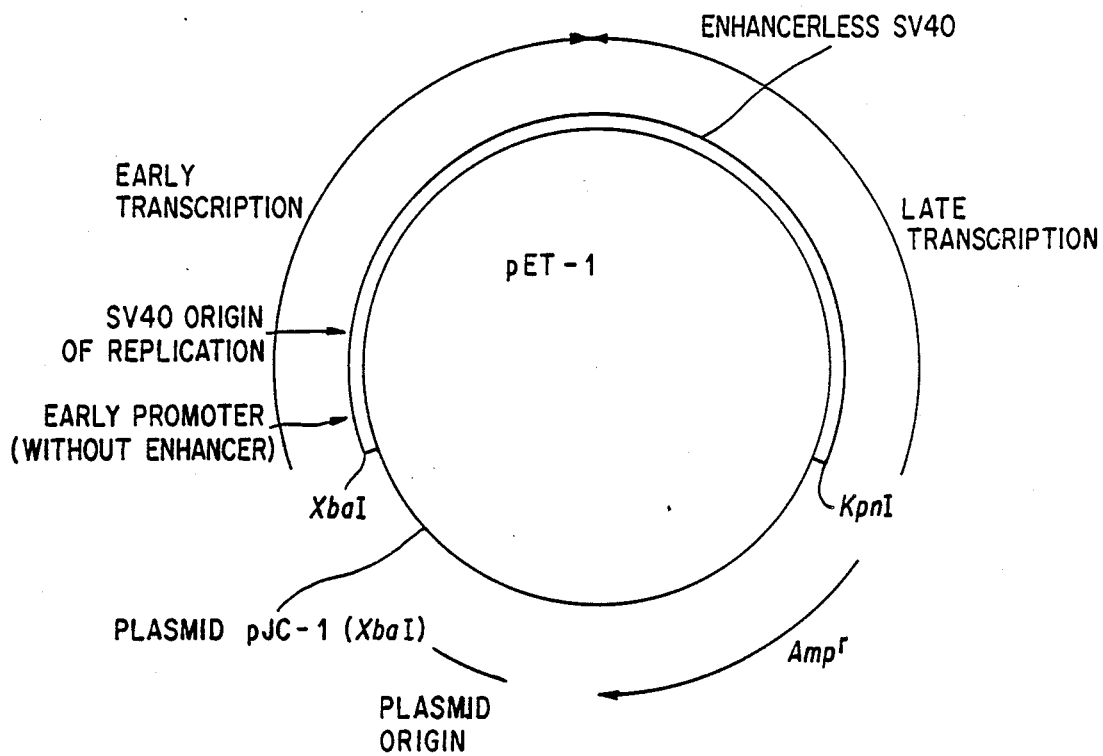

The SV40 enhancer trap clone pET-1 used in the following experiments consists of the large XbaI-KpnI fragment from an SV40 deletion mutant (which contains an XbaI linker DNA insert at SV40 nucleotide position 99) cloned into plasmid pJCl/XbaI (Weber et al ref. 18; FIG. 6). The DNA is prepared by digestion with KpnI and XbaI followed by phenol-extraction, alcohol precipitation (Maniatis et al, ref. 37) and resuspension in TE (10 mM Tris-HCl buffer pH 7.8. plus 1 mM Na-EDTA)

(b) Preparation of MCMV DNA and fragments thereof (i) Isolation of MCMV DNA: Propagation of MCMV in BALB/c mouse fibroblasts and isolation of MCMV DNA are carried out as described by Ebeling et al. (ref. 1), briefly:

Cell culture fluid from infected cells is collected and centrifuged for 20 min at 6.000 rpm in a Beckmann JA10 rotor to eliminate cell debris. The supernatant is removed, and, after centrifugation at 13.000 rpm in a Beckmann JA14 rotor for 3 h, the pellet is suspended in a small volume of phosphate-buffered saline and homogenized by 30 to 50 strokes in a Dounce homogenizer. Cellular DNA is degraded
by incubation with DNase 1 (100 μg/ml) (Boehringer Mannheim, Germany) for 1 h at 37° C. The reaction mixture is layered onto a 15 % sucrose cushion in phosphate-buffeered saline and centrifuged for 1 h at 25.000 rpm in a Beckman SW41 rotor. The resulting pellet is lysed in 2 ml of 20 mM of 20 mM Tris-hydrochloride (pH 8.5) containing 2 % sodium lauroyl sarcosinate and proteinase K (1 mg/ml) (Serva. Heidelberg, Germany) and incubated at 56° C. for 1 h. The lysate is layered onto 8.7 ml of a CsCl solution at a density of 1.832 g/ml and centrifuged to equilibrium at 33,000 rpm for 60 h in a Beckman 50 Ti rotor. The DNA banded at a density of about 1.718 g/ml. Pooled fractions are dialyzed against 20 mM Tris-hydrochloride (pH 8.5), and the final concentration of DNA is determined. EDTA is added to a final concentration of 1 mM. The purity is tested by restriction enzyme digestion.

(ii) Isolation of the 10,8-Kbp Bam HI fragment of MCMV DNA: MCMV DNA is cut with BamHI (Boehringer) and the fragments are inserted into the BamHI site of the plasmid vector pACYC 184 to give rise to plasmid pAMB 25 according to Keil et al (ref. 4). Plasmid DNA is purified from a bacterial clear lysate with cesium chloride-ethidium bromide density gradient centrifugation (Maniatis et al; ref. 37); diluted with water, precipitated by ethanol and dissolved in TE buffer (10 mM Tris-hydrochloride pH=8.0 containing 1 mM Na-EDTA). For cotransfection with enhancer trap pET-1 DNA, pAMB 25 DNA (20 μg in 100 μl TE buffer) was sonicated vigorously (15 times for about 10 sec each with cooling on ice for 30 sec between strokes) such that the majority of the DNA fragments was about 300 bp long.

(iii) Isolation of the 2.27 Kbp PstI fragment of MCMV DNA: The 2.27-Kbp PstI fragment in clone pAMB33 is isolated from pAMB25, cloned into polylinker of pSp62 vector plasmid (ref. 38), prepared (and also sonicated) as described for pAMB 25 DNA.

(iv) Isolation of the XhoI fragment (map units 0.795–0.79): Plasmid pAMB 25 is digested with XhoI and the small XHoI fragment is eluted from a preparation agarose gel (Maniatis et al ref.37) and dissolved in TE.

(c) Transfection of HeLa and monkey CV-1 cells

Cells are transfected with mixtures of pET-1 DNA (digested with XbaI and KpnI) and sonicated MCMV DNA as mentioned under b) by the calcium phosphate technique according to de Villiers et al (ref. 35) and Weber et al. (ref. 18) The MCMV DNAs were used in 10:1 ratio to the pET-1 DNA.

Cells are cultured in Dulbecco's modification of Eagle's minimal essential medium (Gibco), containing 2.5 % fetal calf serum and 2.5 % calf serum, 100 units/ml penicillin and 100 μg/ml streptomycin (Gibco). One day before transfection they are seeded into plastic petri dishes (Falcon) such that they reach ½ to ¾ confluency at the time of transfection. They are fed with 4.5 ml of fresh medium about 4 h before transfection. For each 60 mm dish DNA is coprecipitated with calcium phosphate as follows: 10–15 μg of DNA is diluted to a volume of 210 pl with a solution of 1 mM Tris-HCl, 0.1 mM EDTA (pH 7.8), and the sample is well mixed. Thirty microlitres of a 2 M CaCl₂ solution (CaCl₂×2H₂O, p.a., Merck) are mixed in thoroughly, and the solution cooled to 0° C. on ice. The DNA sample is then added dropwise, within 5–10 s to 240 μl of ice-cold 2 ×Hepes buffered saline (+ phosphate) while agitating, after which it is kept on ice for 90 s. The slightly opaque precipitate is then added to the 4.5 ml medium in the petri dish and the cells are incubcated at 37° C. (One hour after transfection there should be a fine precipitate, with most of the grains being around 1 pm in size, attached to the cells and to the bottom of the dish.) The dishes are washed twice, 16–24 h after transfection, with Tris-buffered saline (TBS, 25 mM Tris-HCl, 137 mM NaCl, 5 mM NaCl, 5 mM KCSl, 0,7 mM CaCl₂, 0.5 mM MgCl₂, 0.6 mM Na₂HPO₄ (pH 7.4) and then incubated with fresh medium. The RNA is extracted 36 h after transfection for S1 nuclease analysis.

(d) Transient expression assay for cytoplasmic RNA

The RNA extraction from transfected cells, either transfected HeLa cells or MCMV-infected mouse cells and the S1 mapping thereof is carried out according to de Villiers et al. (ref. 35).

(i) RNA extraction from transfected cells: Total cellular RNA is extracted after washing the transfected cells twice with TBS (for composition see under (c)). The cells are lysed, after aspirating TBS, in the presence of 400 μg/ml Proteinase K (Merck) by addition of buffer containing 200 mM Tris-HCl (pH 7.5), 25 mM EDTA, 300 mM NaCl and 2 % sodium dodecyl sulphate. After 10 min at room temperature the lysares are transferred to Eppendorf tubes and passed twice through gauge 26 syringe needles to shear the high molecular weight DNA. Incubation at 37° C. for 30 min is followed by extraction with an equilibrated mixture of phenol, chloroform and isoamyl alcohol (50:50:1, containing 0,1 % 8-hydroxyquinoline), and ethanol pecipitation of the nucleic acids. The precipitates are taken up in a small volume (100 μl per $10^6$ cells lysed) of 50 mM Tris-HCl (pH 8). $MgCl_2$ (10 mM) is added and the DNA digested by adding RNAse-free DNAse to a final concentration of 20 pg/ml. After 60 min incubation at 37° C., the samples are again extracted with phenol/-chloroform and ethanol precipitated as before. The precipitates are taken up in a 1 % NaOAc, 0,2 % sodium dodecyl sulphate solution (~500 μl volume per $10^6$ cells lysed) A 250 μl aliquot of 10 M LiCl is added and the mixtures stored for a few hours at 4° C. to precipitate RNA, which is collected by centrifugation. These RNA precipitates are resuspended in TE buffer and the optical density at 260 nm read to estimate the concentration of the solution.

Cytoplasmic RNA is collected by a modification of a previously described technique as obtained in ref. 35. After lysis of the cells, the cell nuclei are pelleted by centrifugation in a bench-top Eppendorf centrifuge and the supernatants, containing the cytoplasmic RNA, are processed further for S1 nuclease mapping.

S1 nuclease mapping using endlabeled double stranded DNA probes is done according to Weaver and Weissmann (ref. 19) and Rusconi and Schaffner (ref. 20).

The specific endlabeled DNA probes are described under (f) and (g).

(e) Isolation and Sequencing of DNA from MCMV-SV40 recombinant viruses containing MCMV enhancer segments.

Cloned enhancerless SV40 DNA (clone pET-1; ref. 18) was cotransfected into monkey kidney CV-1 cells with the following MCMV-specific DNAs: (i) total MCMV DNA isolated from purified virions; (ii) DNA from clone pAMB25, spanning map units 0.769–0.815 of the MCMV genome and coding for the major IE transcript; (iii) DNA from clone pAMB33, spanning map units 0.796–0.806 (FIG. 1) and containing the promoter region of the major IE transcript. In all cases, the CV-1 cells began to lyse 2-3 weeks after transfection indicating that a viable SV40-like virus had been generated. Recombinant SV40-MCMV viral DNAs were isolated and cloned in the bacterial plasmid pBR327. Individual recombinant virus clones were reclaimed from the plasmid and tested for viability by transfection into monkey CV-1 cells using the DEAE-dextran method. Fifteen of 16 clones originating from transfection with the entire MCMV genome, 8 of 8 clones originating from the pAMB25 transfection, and 6 of 8 clones originating from the pAMB33 transfection were viable and lysed CV-1 cells 12-16 days after transfection. This is about the same time it takes to lyse the cells when transfection is performed with SV40 wild-type DNA or SV40-HCMV recombinant DNA (ref. 11).

By Southern blot hybridization it was shown that all the analyzed clones hyridized exclusively to the pAMB33 fragment spanning map units 0.796-0.806 on the MCMV genome indicating that there is a strong enhancer located in the major IE region.

Two such recombinant viruses contained MCMV-derived inserts (P1 and B2) of 311 and 342 bp, respectively. These inserts with flanking SV40 DNA, were sequenced by the method of Maxam and Gilbert (ref. 37) and compared with a region of 885 bp spanning the MCMV enhancer and promotor including the start site of the major immediate early mRNA.

The HindIII C fragments from the recombinant virus clones SV40-MCMV B2 and SV40-MCMV P1 are excised and cloned into the single HindIII site of plasmid pβG (see refs. 26 and 35). Thereby the clones pβG-MCMV B2-8, B2-16, P1-2 were obtained (FIG. 4A).

(f) Analysis of MCMV enhancers by determining activity in human HeLa cells

Quantitative S1 nuclease mapping of rabbit β-globin transcripts in HeLa cells was done as described in ref. 35. A rabbit β-globin gene lacking the first intervening sequence (ref. 27) is end-labeled at BamHI site and used as a radioactive probe.

This probe is hybridized to cytoplasmic RNA from HeLa cells which were transfected with DNA of recombinants B2-8, B2-16, P1-8, and P1-2 DNA (see under (e)).

The hybrid molecules are digested with S1 nuclease, the digestion products are denatured, fractionated by polyacrylamide gel electrophoresis and analyzed by autoradiography.

(g) Determination of initiation site of the major IE RNA of MCMV DNA

Mouse embryo fibroblasts are infected with MCMV. These infected fibroblasts are kept from 0 to 4 hrs in cycloheximide (which results in the accumulation of immediate early RNA) and the RNA is isolated from infected cells (ref. 4).

Cells were trypsinized in the presence of cycloheximide, and about $5 \times 10^7$ cells were washed twice in 50 ml of phosphate-buffered saline-A supplemented with cycloheximide. The cell pellets were lysed in 6 ml of 5.8 M guanidine hydrochloride (Sigma Chemical Co., Munich, Germany) containing 50 mM lithium citrate. 0.1 M β-mercaptoethanol, and 0.5 % Sarkosyl, pH 6.5. The lysate was centrifuged through a 4.5 ml cushion of 5.7 M CsCl in 0.1 M EDTA (pH 7.0) for 22 to 24 h at 32,000 rpm in a Beckman SW41 rotor. The supernatant was carefully decanted, the pellet was resuspended in distilled water, and 0.2 volume of 1 M potassium acetate was added. RNA was precipitated with 2.5 volumes of ethanol at −20° C. The precipitate was collected by centrifugation, washed twice with 70 % ethanol, and dried under vacuum. The RNA was resuspended in a small volume of distilled water and stored at −70° C. Polyadenylated [poly(A)+] RNA was selected from total RNA by oligodeoxythymidylic acid-cellulose chromatography (BRL, Neu Isenburg, Germany) following published procedures (ref. 15). 10 μg RNA was hybridized to the end-labeled single stranded MCMV XhoI fragment spanning map units 0.795–0.797 (see FIG. 1). The hybrids were digested with S1 nuclease, denatured, fractionated by gel electrophoresis and subjected to autoradiography. Lanes: 1. hybridization of the single stranded XhoI fragment to IE RNA; 2. the same probe hybridized to RNA from uninfected mouse 3T3 cells; 3. the opposite strand of the end-labeled XhoI fragment hybridized to MCMV IE RNA; 4. full length probe; M. DNA marker (see FIG. 4).

FIGURE LEGENDS

FIG. 1

A: HindIII restriction map of the MCMV genome.

B: The region encoding the 2.75-kb major immediate early transcript is expanded. The 10.8-kb BamHI fragment (clone pAMB25) and the 2.27-kb PstI fragment (clone pAMB33) were used together with enhancer trap DNA for cotransfection into monkey CV-1 cells. The XhoI fragment spanning map units 0.795–0.797 was used to determine the site of IE RNA initiation by S1 nuclease analysis. The direction of transcription of the 2.75-kb IE RNA is indicated by an arrow.

FIG. 2

The SV40 enhancer trap experiment (A) HindIII C fragment of wild type SV40 (nucleotide positions 5171–1046 of the SV40 map, ref. 22). This fragment encompasses the origin of DNA replication, the major initiation site of early RNA and the enhancer. The 21/22-bp repeats and the 72-bp repeats are shown by bold arrows. The SV40 enhancer trap clone pET-1 is an enhancer deletion mutant (nucleotides 99–294 are deleted) and has an XbaI restriction site inserted at position 99 (ref. 18).

(B) HindIII C fragment from the recombinant SV40-MCMV P1 clone containing the MCMV enhancer. It originated from cotransfection of enhancer trap DNA and the MCMV-specific 2.27 kb pAMB33 fragment into CV-1 cells. The inserted MCMV sequence is 311 bp long. At the XbaI site, the XbaI linker and four nucleotides of SV40 DNA are deleted; at the KpnI site 11 nucleotides of SV40 DNA are deleted.

(C) HindIII C fragment from the recombinant SV40-MCMV B2 clone. It was obtained by cotransfection of enhancer trap molecules with the MCMV-specific 10.8-kb pAMB25 fragment to CV-1 cells. The MCMV insertion is 342 bp long and is inserted between the XbaI linker and the KpnI site, where 14 nucleotides of SV40 DNA are deleted. The sequence overlapping in the MCMV enhancer segments present in the two recombinant clones is shown by black bars.

(D) Map of the SV40 genome indicating the direction of early and late transcription units.

FIG. 3 A

Sequence of the MCMV enhancer and its flanking regions. The MCMV specific enhancer sequence contained in the recombinant SV40-MCMV viruses B2 and P1 is indicated. The cap site is marked by "+1".

FIG. 3 B

Schematic presentation of the repeat structure of the MCMV enhancer and its flanking region. The enhancer segments in recombinants B2 and P1 are indicated by bars, and the direct sequence repeats are indicated by arrows.

Several classes of direct repeats are noteworthy: (a) Two sequences, 181 bp and 180 bp long (positions −668 to −487, and −482 to −302). are 92 % homologous to each other. (b) One 130 bp sequence (position −872 to −698) is 92 % homologous to the 181 bp sequence and 95 % homologous to the 180 bp sequence. (c) Five 51 bp repeats (dashed lines); the two far upstream ones are 100 % homologous to each other; the others are 92 % to 98 % homologous to the first two. All five 51-bp repeats are contained within the 130, 180 and 181 bp repeated sequences.

FIG. 4

Functional analysis of the MCMV enhancer (A) To test the strength of the MCMV enhancer, the HindIII C fragments from the recombinants B2 and P1 (FIG. 2) containing the MCMV enhancer were inserted downstream of the rabbit $\beta$-globin gene in the HindIII site of clone p$\beta$G (ref. 26 and 35) in either orientation. The closed circle indicates the position of the SV40 origin of replication.

(B) S1 nuclease assay. A $\beta$-globin gene clone lacking the first intervening sequence (ref. 27) was end-labeled at the BamHl site. The single-stranded probe was hybridized to 20 $\mu$g cytoplasmic RNA that had been isolated from HeLa cells transfected with the enhancer-containing pBG clones. The hybrids were digested with S1 nuclease, denatured, analyzed by gel electrophoresis and autoradiographed. Lanes: 1. p$\beta$G-WT3 contains the HindIII C fragment of SV40 wild-type DNA inserted downstream of the rabbit $\beta$-globin gene; 2. p$\beta$G-HCAE, contains the HindIII fragment from reclosed viral enhancer trap DNA lacking the enhancer sequence; 3. p$\beta$G-MCMV B2-8; 4. p$\beta$G-MCMV B2-16; 5. p$\beta$G-MCMV P1-8; 6. p$\beta$G-MCMV P1-2; 7. HCMV enhancer C4 located downstream of the rabbit $\beta$-globin gene (ref. 11); 8. full-length probe (453 nucleotides); 9. p$\beta$G-MCMV B2-8, the same clone as in lane 3, but a different plasmid preparation was used for transfection. The sequences protected from S nuclease digestion are 354 nucleotides long; M. DNA marker (Plasmid pBR322 cleaved with HpaII).

FIG. 5

Initiation site of the major IE RNA. Cytoplasmic RNA was isolated 4 hours after infection from mouse embryo fibroblasts infected with MCMV in the presence of cycloheximide (ref. 4). 10 $\mu$g RNA was hybridized to the end-labeled single-stranded MCMV XhoI fragment spanning map units 0.795–0.797 (see FIG. 1). The hybrids were digested with S1 nuclease, denatured, fractionated by gel electrophoresis and subjected to autoradiography. Lanes: 1. hybridization of the single stranded XhoI fragment to IE RNA; 2. the same probe hybridized to RNA from uninfected mouse 3T6 cells; 3. the opposite strand of the end-labeled XhoI fragment hybridized to MCMV IE RNA; 4. full length probe; M. DNA marker (see FIG. 4).

FIG. 6

Structure of the plasmid pET-1

The SV40 enhancer trap molecule is liberated from the pJC-1 (Xba) plasmid by double digestion with KpaI and XbaI.

The enhancerless SV40 DNA can also be grown in other plasmids which contain a XbaI and a KpnI site.

1. Ebeling, A., Keil, G.M., Knust, E. & Koszinowski, U.H. (1983) J. Virol. 47, 421-433.
2. Mercer, J.A., Marks, J. R. & Spector, D. H. (1983) Virology 129, 94-106.

3. Marks, J.R., Mercer, J. A. & Spector, D. H. (1983) Virology 131, 247–254.
4. Keil, G.M., Ebeling-Keil, A. & Koszinowski, U. H. (1984) J. Virol. 50, 784–795.
5. Banerji, J., Rusconi, S. & Schaffner, W. (1981) Cell 27, 299–308.
6. Moreau, P., Hen.R., Wasylyk, B., Everett, R., Gau, M. P. & Chambon, P. (1981) Nucleic Acids Res. 9, 6047–6068.
7. Picard, D. (1985) Oxford Surveys of Eucaryotic Genes (Oxford Univ. Press, London), Vol. 2. pp. 24–47.
8. Gluzman, Y., ed. (1985) Eukaryotic Transcription: The Role of cis- and trans-Acting Elements in Initiation (Cold Spring Harbor Laboratory, Cold Spring Harbor, NY).
9. Serfling, E., Jasin, M. & Schaffner, W. (1985) Trends in Genetics.
10. Lang, J.C., Spandidos, D. M. & Wilkie, N. M. (1984) EMBO J. 3, 389–395.
11. Boshart, M., Weber, F., Jahn, G., Dorsch-Häsler, K., Fleckenstein, B. & Schaffner, W. (1985) Cell 41, 521–530.
12. Schirm, S., Weber, F., Schaffner, W. & Fleckenstein, B. (1985) EMBO J., in press. 4, 2665–2674.
13. Banerji, J., Olson, L. & Schaffner, W. (1983) Cell 33, 729–740.
14. Gillies, S.D., Morrison, S.L., Oi, V. T. & Tonegawa, S. (1983) Cell 33, 717–728.
15. Picard, D. & Schaffner, W. (1984) Nature (London) 307, 80–82.
16. Walker, M.D., Cell, in press. et. al (1973) Nature 306, 357–361.
17. Gillies, S.D., Folsom, V. & Tonegawa, S. (1984) Nature (London) 310, 594–597.
18. Weber, F., de Villiers, J. & Schaffner, W. (1984) Cell 36 983–992.
19. Weaver, R. F. & Weissmann, C. (1979) Nucleic Acids Res. 7, 1175–1193.
20. Rusconi, S. & Schaffner, W. (1981) Proc. Natl. Acad. Sci. USA 78, 5051–5055.
21. Hearing. P. & Shenk, T. (1983) Cell 33, 695–703.
22. Tooze, J., ed. (1981) DNA Tumor Viruses (Cold Spring Harbor Laboratory, Cold Spring Harbor, NY).
23. Efstratiadis, A., Posakony. J. W., Maniatis, T., Lawn. R. M., O'Connell, C., Spritz, R.A., DeReil, J. K., Forget, B. G. P., Weissmann, S.M., Slightom, J.L., Blechi, A.E., Smithies, 0., Baralle, F.E., Shoulders, C.C. & Proudfoot, N,J. (1980) Cell 21, 653–668.
24. McKnight, S.L., Kingsbury, R.C., Spence, A. & Smith, M. (1984) Cell 37, 253–262.
25. Everett, R.D., Baty, D. & Chambon, P. (1983) Nucleic Acids Res. 11, 2447–2464.
26. de Villiers, J., Olson, L., Tyndall, C. & Schaffner. W. (1982) Nucleic Acids Res. 10, 7965–7975.
27. Weber, H., Dierks, P., Meyer, F., van Ooyen, A., Dobkin, C., Abrescia, P., Kappeler, M., Meyhack, B., Zeltner, A., Mullen, E.E. & Weissmann, C. (1981) ICN-UCLA Sympl Mol. Cell. Biol. 33, 367–385.
28. Weber, F. & Schaffner, W. (1985) EMBO J. 4, 949–956.
29. Weiher, H., König, M & Gruss, P. (1983) Science 219 626–631.
30. Gidoni, D., Dynan, W.S. & Tijan, R. (1984) Nature (London) 312, 409–413.
31. Dierks, P., van Ooyen, A., Cochran, M.D., Dobkin, C., Reiser, J. & Weissman, C (1983) Cell 32, 695–706.
32. Stuart, G.W., Searle, P.F., Chen, H.Y., Brinster, R.L. & Palmiter, R.D. (1984) Proc. Natl. Acad. Sci. USA 81, 7318–7322.
33. Carter. A.D., Felber, B.K., Walling, M.J., Jubier, M.F., Schmidt, C.J. & Hamer, D.H. (1984) Proc. Natl. Acad. Si. USA 81, 7392–7396.
34. Tognoni, A., Cattaneo, R., Serfling E. & Schaffner, W. (1985). Nucl. Acids Res. 13, 7457–7472.
35. de Villiers, J. & Schaffner, W. (1983). (review article). In: Techniques in the Life Sciences, (B5) Nucleic Acid Biochemistry, Ed. Flavell, R.A. Elsevier Scientific Publishers Irelands, Ltd., 1–20.
36. Maniatis, T., Fritsch, E.F., and Sambrook, J. (1982). Molecular Cloning (A Laboratory Manual). (Cold Spring Harbor, New York: Cold Spring Harbor Laboratory).
37. Maxam, A.M., and Gilbert, W. (1980). Sequencing end-labelled DNA with base-specific chemical cleavages. Meth. Enzymol. 65, 499–560.
38. Krieg P.A. & Melton D.A. (1984) Nature 308, (1984) 203–206

What is claimed is:

1. A DNA fragment from murine cytomegalovirus containing transcription enhancer DNA from the upstream region of the major immediate early (IE) gene of murine cytomegalovirus (MCMV) or an enhancer-active mutant thereof, and optionally promoter sequences or other flanking sequences.

2. A DNA fragment according to claim 1 containing the PstI restriction fragment located between 0.806 and 0.796 map units of the MCMV genome.

3. A DNA fragment containing the HindIII C fragment from the recombinant SV40-MCMV P1 clone (of FIG. 2, B) containing the MCMV enhancer which originates from a cotransfection of SV40 enhancer trap DNA and the MCMV-specific 2.27-kb PstI fragment of the MCMV genome, according to claim 1.

4. A DNA fragment containing the HindIII C fragment from the recombinant SV40-MCMV B2 clone (of FIG. 2, C) containing the MCMV enhancer which originates from a cotransfection of SV40 enhancer trap DNA and the MCMV-specific 10.8-kb PstI fragment of the MCMV genome, according to claim 1.

5. A DNA fragment containing the DNA sequence of the formula

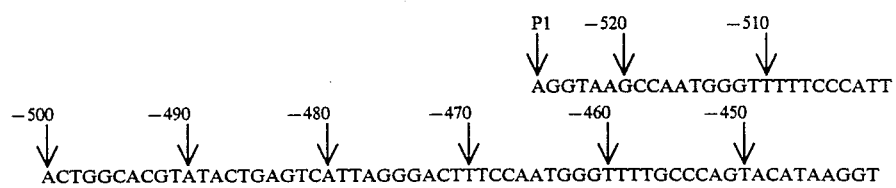

```
       -440         -430         -420         -410         -400         -390
        ↓            ↓            ↓            ↓            ↓            ↓
            CAATAGGGGTGAATCAACAGGAAAGTCCCATTGGAGCCAAGTACACTGAGTCAATAGGGA
       -380         -370         -360         -350         -340         -330
        ↓            ↓            ↓            ↓            ↓            ↓
            CTTTCCATTGGGTTTTGCCCAGTACAAAAGGTCAATAGGGGGTGAGTCAATGGGTTTTTC
       -320         -310         -300         -290         -280         -270
        ↓            ↓            ↓            ↓            ↓            ↓
            CCATTATTGGCACGTACATAAGGTCAATAGGGGTGAGTCATTGGGTTTTTCCAGCCAATT
       -260         -250         -240         -230         -220    P1
        ↓            ↓            ↓            ↓            ↓   ↓
            TAATTAAAACGCCATGTACTTTCCCACCATTGACGTCAATGGGCT,
``` according to claim 1.

6. A DNA fragment containing the DNA sequence of the formula

```
                                                                        B2
                                                                        ↓
                                                                        GT
       -440         -430         -420         -410         -400         -390
        ↓            ↓            ↓            ↓            ↓            ↓
            CAATAGGGGTGAATCAACAGGAAAGTCCCATTGGAGCCAAGTACACTGAGTCAATAGGGA
       -380         -370         -360         -350         -340         -330
        ↓            ↓            ↓            ↓            ↓            ↓
            CTTTCCATTGGGTTTTGCCCAGTACAAAAGGTCAATAGGGGGTGAGTCAATGGGTTTTTC
       -320         -310         -300         -290         -280         -270
        ↓            ↓            ↓            ↓            ↓            ↓
            CCATTATTGGCACGTACATAAGGTCAATAGGGGTGAGTCATTGGGTTTTTCCAGCCAATT
       -260         -250         -240         -230         -220         -210
        ↓            ↓            ↓            ↓            ↓            ↓
            TAATTAAAACGCCATGTACTTTCCCACCATTGACGTCAATGGGCTATTGAAACTAATGCA
       -200         -190         -180         -170         -160         -150
        ↓            ↓            ↓            ↓            ↓            ↓
            ACGTGACCTTTAAACGGTACTTTCCCATAGCTGATTAATGGGAAAGTACCGTTCTCGAGC
       -140         -130         -120         -110         B1
        ↓            ↓            ↓            ↓           ↓                o
            CAATACACGTCAATGGGAAGTGAAAGGGCAGCCAAAACGT,
``` according to claim 1.

7. A DNA fragment according to claim 1 which contains the MCMV IE promoter.

8. A DNA fragment according to claim 1 which contains a linker sequence.

9. A DNA fragment according to claim 1 which contains a signal sequence.

10. Process for the production of a DNA molecule containing transcription enhancer DNA from the upstream region of the major immediate early (IE) gene of murine cytomegalovirus (MCMV) or an enhancer-active mutant thereof, and optionally promoter sequences or other flanking sequences, characterized in (a) fragmenting DNA molecules from the IE region of MCMV or purified total MCMV, cotransfecting the obtained DNA fragments with enhancerless genomes of another virus into eukaryotic cells, isolating from the transfected cells viable recombinant viruses containing DNA molecules showing enhancer activity and isolating from the obtained viral DNA the inserted DNA originating from MCMV, or (b) determining the structure of the inserted MCMV DNA molecule and synthesizing the inserted MCMV DNA molecule, an enhancer-active fragment or enhancer-active mutant thereof, (c) or fragmenting purified total MCMV DNA or DNA molecules from the IE region of the MCMV DNA by sonication or by treatment with at least one restriction enzyme or optionally an exonuclease, optionally followed by treatment with a DNA polymerase, optionally followed by cloning in a suitable vector, whereby the enhancer DNA is identified by hybridization to DNA containing a sequence of the IE enhancer or IE promoter.

11. A recombinant DNA molecule containing transcription enhancer DNA from the upstream region or the major immediate early (IE) gene of murine cytomegalovirus (MCMV) or an enhanceractive mutant thereof, and optionally promoter sequences or other flanking sequences.

12. A recombinant DNA molecule according to claim 11 containing the PstI restriction fragment located between 0.806 and 0.796 map units of the MCMV genome.

13. A recombinant DNA molecule according to claim 11 containing the DNA sequence of the formula

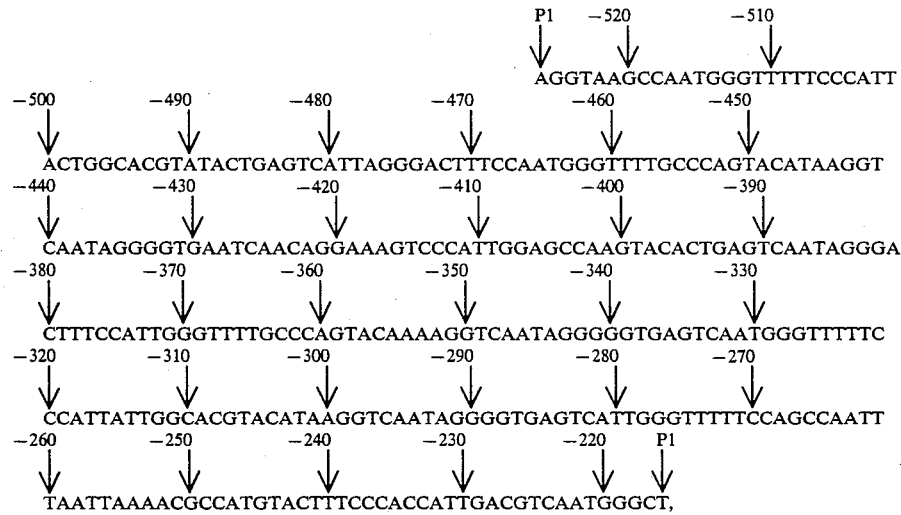

14. A recombinant DNA molecule according to claim 11 containing the DNA sequence of the formula

19. A recombinant DNA molecule according to claim 11 which contains the MCMV IE promoter.

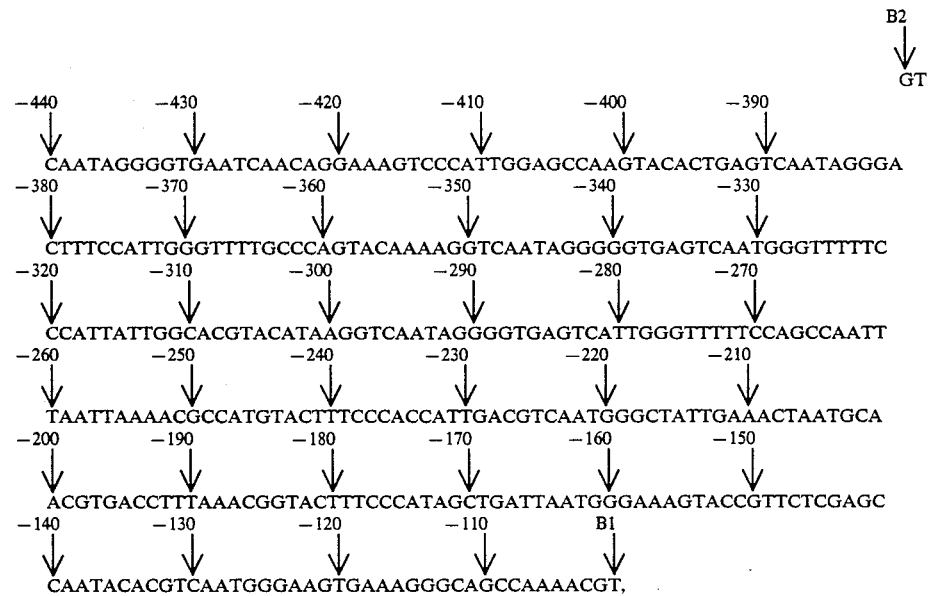

15. A recombinant DNA molecule according to claim 11 which contains a heterologous eukaryotic promoter.

16. A recombinant DNA molecule according to claim 11 which contains a heterologous structural gene.

17. A recombinant DNA molecule according to claim 11 containing the HindIII C fragment from the recombinant SV40-MCMV P1 clone of FIG. 2, B containing the MCMV enhancer which originates from a cotransfection of SV40 enhancer trap DNA and the MCMV-specific 2.27-kb PstI fragment of the MCMV genome.

18. A recombinant DNA molecule according to claim 11 containing the HindII C fragment from the recombinant SV40-MCMV B2 clone of FIG. 2,C containing the MCMV enhancer which originates from a cotransfection of SV40 enhancer trap DNA and the MCMV-specific 10.8-kb PstI fragment of the MCMV genome.

20. A recombinant DNA molecule according to claim 11 which contains a linker sequence.

21. A recombinant DNA molecule according to claim 11 which contains a signal sequence.

22. A recombinant DNA molecule with comprise a nucleotide sequence encoding to heterologous protein operatively linked to the approximately 2.27 kilobase pair PstI restriction, fragment of the MCMV genome containing the mouse cytomegalovirus (MCMV) immediate early promoter or to an effective expression promoting fragment thereof.

23. A process for the production of a recombinant DNA molecule containing transcription enhancer DNA from the upstream region of the major immediate early (IE) gene of murine cytomegalovirus (MCMV) or an enhancer-active mutant thereof, and optionally promoter sequences or other flanking sequences, which process comprises the steps of claim 10 followed by preparing a recombinant DNA molecule containing the obtainable transcription enhancer DNA or enhancer-active mutant thereof.

24. A process for improving eukaryotic expression systems, which comprises incorporation of a DNA molecule containing transcription enhancer DNA from the upstream region of the major immediate early (IE) gene of murine cytomegalovirus (MCMV) or an enhancer active mutant thereof upstream or downstream of a structural gene or of the regulation region.

25. A process for improving eukaryotic expression systems, which comprises incorporation of a DNA molecule containing transcription enhancer DNA from the upstream region of the major immediate early (IE) gene of murine cytomegalovirus (MCMV) or an enhancer-active mutant thereof upstream or downstream of a structural gene or of the regulation region.

* * * * *